(12) United States Patent
Iwagaki et al.

(10) Patent No.: US 10,058,161 B2
(45) Date of Patent: Aug. 28, 2018

(54) DOUBLE EYELID FORMATION TAPE, METHOD FOR MANUFACTURING SAME, AND METHOD FOR FORMING DOUBLE EYELID USING DOUBLE EYELID FORMATION TAPE

(71) Applicant: artsbrains. co. Ltd., Shibuya-ku (JP)

(72) Inventors: Naoko Iwagaki, Fujimino (JP); Masayuki Kamagata, Sanbu-gun (JP); Jirou Taniyama, Yokohama (JP)

(73) Assignee: artsbrains.co. Ltd., Shibuya-ku (JP)

( * ) Notice: Subject to any disclaimer, the term of this patent is extended or adjusted under 35 U.S.C. 154(b) by 348 days.

(21) Appl. No.: 14/786,398

(22) PCT Filed: Apr. 17, 2014

(86) PCT No.: PCT/JP2014/060918
§ 371 (c)(1),
(2) Date: Oct. 22, 2015

(87) PCT Pub. No.: WO2014/175159
PCT Pub. Date: Oct. 30, 2014

(65) Prior Publication Data
US 2016/0073768 A1    Mar. 17, 2016

(30) Foreign Application Priority Data

Apr. 23, 2013  (JP) .................................. 2013-090486

(51) Int. Cl.
*A45D 44/22* (2006.01)
*A61F 9/007* (2006.01)

(52) U.S. Cl.
CPC .......... *A45D 44/22* (2013.01); *A61F 9/00718* (2013.01)

(58) Field of Classification Search
CPC ........... C09J 5/00; C09J 7/0253; A45D 44/22; A45D 44/00; Y10T 428/14; Y10T 428/28;
(Continued)

(56) References Cited

U.S. PATENT DOCUMENTS 5,582,585 A * 12/1996 Nash-Morgan ........ A45D 44/22
                                                                428/343
6,733,856 B2 * 5/2004 Nojiri .................... A45D 44/00
                                                                132/216
8,617,199 B2 * 12/2013 Eull .......................... A61F 5/08
                                                                606/199

FOREIGN PATENT DOCUMENTS

JP           2-188512 A       7/1990
JP          10-304935 A      11/1998
(Continued)

OTHER PUBLICATIONS

International Search Report dated Jul. 22, 2014 in PCT/JP2014/060918 filed Apr. 17, 2014.
(Continued)

*Primary Examiner* — Patricia L. Nordmeyer
(74) *Attorney, Agent, or Firm* — Oblon, McClelland, Maier & Neustadt, L.L.P.

(57) ABSTRACT

A double eyelid formation tape is formed by applying an adhesive, which is used for attaching a tape-shaped member to an eyelid, to the tape-shaped member, which has a long length and which has elastic contractility when the tape-shaped member is stretched to a predetermined length in a longitudinal direction, and that is used for forming a double eyelid by utilizing the elastic contractility of the tape-shaped member. The tape-shaped member is formed of a multilayer body that includes a first base material layer made of a polyethylene and a second base material layer made of polyurethane. When the tape-shaped member is stretched to the predetermined length, the first base material layer is
(Continued)

caused to transition to the plastic zone and is configured to have elastic contractility even in the plastic zone.

16 Claims, 7 Drawing Sheets

(58) Field of Classification Search
CPC ......... Y10T 428/1486; Y10T 428/1457; Y10T 428/1476; A61F 9/00718
See application file for complete search history.

(56) References Cited

FOREIGN PATENT DOCUMENTS

| | | |
|---|---|---|
| JP | 3277180 B1 | 4/2002 |
| JP | 3111511 U | 7/2005 |
| JP | 2005-334108 A | 12/2005 |
| JP | 2007-106711 A | 4/2007 |
| JP | 2007-111218 A | 5/2007 |
| JP | 2009-22592 A | 2/2009 |
| JP | 2009-195410 A | 9/2009 |
| JP | 3154139 U | 10/2009 |
| JP | 2012-223250 A | 11/2012 |

OTHER PUBLICATIONS

Office Action dated Jun. 14, 2016 in Japanese Patent Application No. 2013-090486 (with English language translation).

\* cited by examiner

DOUBLE EYELID FORMATION TAPE, METHOD FOR MANUFACTURING SAME, AND METHOD FOR FORMING DOUBLE EYELID USING DOUBLE EYELID FORMATION TAPE

TECHNICAL FIELD

The present invention relates to a double eyelid formation tape that is used for forming a double eyelid by utilizing elastic contractility of a tape-shaped member, which is obtained when the tape-shaped member is stretched, a method for manufacturing the double eyelid formation tape, and a method for forming a double eyelid using the double eyelid formation tape.

BACKGROUND ART

In the related art, as examples of double eyelid forming cosmetics, which are used for causing a single eyelid to become a pseudo-double eyelid without a surgical operation, solution-type double eyelid forming cosmetics (Patent Documents 1 to 3) each of which is a solution to be used by being applied on a skin of an eyelid and tape-type double eyelid forming cosmetics (Patent Documents 4 to 8) each of which is an adhesive tape to be used by being attached to a skin of an eyelid are known.

These solution-type and tape-type double eyelid forming cosmetics can be classified in terms of how to form a double eyelid and are classified primarily into a method (bonding method) of forming a fold of a double eyelid by bonding portions of a skin of an eyelid together with a double-sided adhesive tape, an adhesive, or the like in a state where the eyelid is folded and a method (shutter method) of forming a coating, which is harder than a skin of an eyelid, on the skin of the eyelid by, for example, applying a solution to the skin of the eyelid and drying the solution or by attaching an adhesive tape to the skin of the eyelid, so that when opening the eyelid, the skin is folded back along the upper edge of the coating, and a fold of a double eyelid is formed.

However, since these double eyelid forming cosmetics of the related art are used for forcibly forming a fold of a double eyelid by utilizing such bonding using a solution or a tape and such a coating, there have been problems, for example, in that a fold of a double eyelid to be formed is likely to be unnatural, it is likely that these double eyelid forming cosmetics will be noticed when they are used, and a user is likely to feel an uncomfortable feeling, such as twitching feeling.

Accordingly, in order to solve the above problems, the applicant has proposed a double eyelid formation tape (Patent Document 9) with which a double eyelid can be formed by a method completely different from methods of the related art. This double eyelid formation tape causes an eyelid to contract by utilizing elastic contractility of a base material tape, which is made of a synthetic resin, that is obtained after the base material tape has been extended (after the base material tape has transitioned to the plastic zone as a result of being stretched) so that a neck portion that follows the shape of the base material tape and has a recessed groove shape is formed in the eyelid. As a result, when opening the eyelid, the eyelid is naturally folded back at the neck portion, and a fold of a double eyelid is formed. According to the double eyelid formation tape employing the new method, a double eyelid, which is more natural, can be formed without providing an uncomfortable feeling to a user by an extremely simple operation, the operation including stretching the base material tape by holding end portions of the base material tape, attaching the base material tape to an eyelid by pressing the base material tape against the eyelid while the base material tape is stretched, and releasing the end portions. In addition, the double eyelid formation tape is excellent in terms of convenience and operability for the following reasons. The double eyelid formation tape can be compactly stored before use, and when the double eyelid formation tape is used, the elastic contractility that contributes to formation of a double eyelid can be obtained by extending the base material tape by pulling the base material tape. The double eyelid formation tape can be easily attached to an eyelid because the double eyelid formation tape is pressed against the eyelid while the base material tape, which has been extended, is maintained in a pulled state. Furthermore, the double eyelid formation tape has an advantage, for example, in that, in a state where the double eyelid formation tape is attached to an eyelid, the base material tape that has become thin as a result of being extended is positioned in a neck portion formed in the eyelid, and thus, it is not likely that the double eyelid formation tape, which is attached to the eyelid, will be noticed.

The states of human eyelids normally differ between individuals, and for example, there are eyelids each of which is less likely to become a double eyelid because of a thick layer of fat or the like and eyelids each of which will easily become a double eyelid even if the eyelid is a single eyelid. Therefore, it is desirable that the double eyelid formation tape, which has been previously proposed and which employs the new method, can be widely used for such eyelids in various states while making good use of its excellent advantages.

CITATION LIST

Patent Document

Patent Document 1: Japanese Unexamined Patent Application Publication No. 2007-106711
Patent Document 2: Japanese Registered Utility Model No. 3111511
Patent Document 3: Japanese Unexamined Patent Application Publication No. 02-188512
Patent Document 4: Japanese Registered Utility Model No. 3154139
Patent Document 5: Japanese Unexamined Patent Application Publication No. 10-304935
Patent Document 6: Japanese Unexamined Patent Application Publication No. 2005-334108
Patent Document 7: Japanese Unexamined Patent Application Publication No. 2007-111218
Patent Document 8: Japanese Unexamined Patent Application Publication No. 2009-195410
Patent Document 9: Japanese Patent No. 3277180

SUMMARY OF INVENTION

Technical Problem

Accordingly, it is an object of the present invention to provide an improved double eyelid formation tape that can be more widely used for eyelids in various states while making good use of its excellent advantages that utilize elastic contractility of a synthetic resin tape, which is obtained after the synthetic resin tape has been extended, a method for manufacturing the double eyelid formation tape, and a method for forming a double eyelid using the double eyelid formation tape.

Solution to Problem

To solve the above described problems, a double eyelid formation tape according to the present invention is formed by applying a first adhesive, which is used for attaching a tape-shaped member to an eyelid, to two surfaces or one surface of the tape-shaped member, which has a long length and which has elastic contractility when the tape-shaped member is stretched to a predetermined length in a longitudinal direction of the tape-shaped member, and that is used for forming a double eyelid by utilizing the elastic contractility of the tape-shaped member. The tape-shaped member is formed of a multilayer body that includes a first base material layer, which is made of a synthetic resin other than an elastomer resin, and a second base material layer, which is made of an elastomer resin, and when the tape-shaped member is stretched to the predetermined length, the first base material layer is caused to transition to a plastic zone and has elastic contractility even in the plastic zone.

In this case, it is preferable that, when the tape-shaped member is stretched to the predetermined length, the first base material layer have a maximum elastic contractive force larger than that of the second base material layer.

In the double eyelid formation tape, it is preferable that the synthetic resin be polyolefin, and it is more preferable that the synthetic resin and the elastomer resin respectively be a polyethylene and polyurethane. Necking may occur in the first base material layer in the plastic zone.

In the double eyelid formation tape, it is desirable that an axis of the tape-shaped member linearly extend in the longitudinal direction. The tape-shaped member may be formed of a multilayer body that is formed by bonding the first and second base material layers together with a second adhesive. In this case, the first base material layer may be made of the synthetic resin in a single layer and has a first surface and a second surface, which is opposite to the first surface, the second base material layer may be made of the elastomer resin in a single layer and has a first surface and a second surface, which is opposite to the first surface, the first adhesive may be applied to the first surface of the first base material layer and/or the second surface of the second base material layer, and the tape-shaped member may be formed of a multilayer body that includes the first and second base material layers and that is formed by bonding the second surface of the first base material layer and the first surface of the second base material layer together with the second adhesive.

In the double eyelid formation tape, a pair of nonviscous holding portions that are to be held and pulled can be formed in end portions of the tape-shaped member in the longitudinal direction. More specifically, the double eyelid formation tape further includes a release sheet piece that has a property of being easily released from an adhesive, and the release sheet piece is attached to the first adhesive of the tape-shaped member and has an easily-tearable portion formed in a center portion of the release sheet piece in a longitudinal direction of the release sheet piece, the easily-tearable portion being configured to be easily torn as a result of being pulled in the longitudinal direction, and the pair of holding portions are formed of end portions of the release sheet piece on opposite sides of the easily-tearable portion in the longitudinal direction. When the tape-shaped member is pulled in the longitudinal direction by holding the pair of holding portions, the release sheet piece tears at the easily-tearable portion, and an intermediate portion of the release sheet piece, which is positioned between the pair of holding portions, separates from the first adhesive. In this case, it is desirable that the release sheet piece be made of a silicone resin, and that the easily-tearable portion be formed of a linear score that is formed by cutting the release sheet piece from an inner surface of the release sheet piece, which is in contact with the first adhesive, to halfway through the release sheet piece in a thickness direction and that extends in a lateral direction.

The double eyelid formation tape can be manufactured by a method including (1) a step of preparing an adhesive sheet that is formed by applying the first adhesive to two surfaces or one surface of a multilayer body that includes a first base material sheet made of the synthetic resin and a second base material sheet made of an elastomer resin and (2) a step of manufacturing the double eyelid formation tape by cutting the adhesive sheet into an elongated belt-like shape.

In this case, it is preferable that the synthetic resin be polyolefin.

In particular, the double eyelid formation tape that includes the release sheet piece can be manufactured by a method including (1) a step of preparing an adhesive sheet that is formed by applying the first adhesive to two surfaces or one surface of a multilayer body that includes a first base material sheet made of the synthetic resin and a second base material sheet made of an elastomer resin, (2) a step of preparing a release sheet that has a property of being easily released from an adhesive and that includes the easily-tearable portion, (3) a step of manufacturing a multilayer sheet that is formed by attaching the release sheet to the first adhesive of the adhesive sheet, and (4) a step of manufacturing the double eyelid formation tape by cutting the multilayer sheet into an elongated belt-like shape in such a manner that the easily-tearable portion is positioned in a middle in a longitudinal direction.

In this case, it is preferable that the method further include a step of forming the easily-tearable portion by forming a linear score extending from an inner surface of the release sheet piece, which is in contact with the first adhesive, to halfway through the release sheet piece in a thickness direction. It is preferable that the synthetic resin be polyolefin, and it is preferable that the release sheet be made of a silicone resin.

According to the double eyelid formation tape, a double eyelid can be formed by a method including (1) a step of attaching the tape-shaped member to an eyelid with the first adhesive by holding and pulling end portions of the tape-shaped member in the longitudinal direction of the tape-shaped member and pressing the tape-shaped member against the eyelid in a state where the tape-shaped member is stretched to the predetermined length, (2) a step of forming a neck portion that follows a shape of the tape-shaped member and has a recessed groove shape in the eyelid by removing a force that pulls the tape-shaped member, which has been attached to the eyelid, and causing the eyelid to contract due to elastic contraction of the tape-shaped member, and (3) a step of forming a fold of a double eyelid as a result of the eyelid being folded back at the neck portion when the eyelid is opened.

Advantageous Effects of Invention

According to the present invention, excellent advantages of a double eyelid formation tape, which has been previously proposed can be exploited by a first base material layer that is made of a synthetic resin, that is caused to transition to the plastic zone when a tape-shaped member is stretched to a predetermined length, and that has elastic contractility even in the plastic zone. In addition, a second base material layer that is made of an elastomer resin and that has an excellent elastic contraction characteristic when the second base material layer is stretched is stacked on the first base material layer, so that an elastic contractive force and an elastic contraction percentage with which tape-shaped member can contract by resisting the large tension of an eyelid that is less likely to become a double eyelid and form a neck portion having a necessary depth while an increase in the cross-sectional areas of the base material layers of the tape-shaped member is suppressed can be obtained.

DESCRIPTION OF EMBODIMENTS

A double eyelid formation tape according to an embodiment of the present invention will be described in detail below with reference to the drawings.

Figure 1:
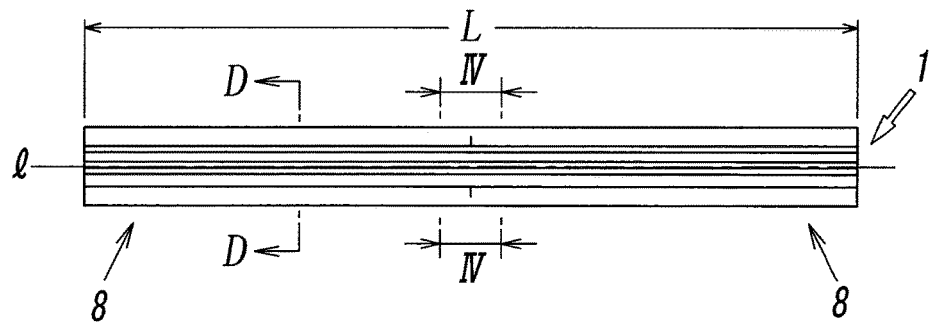
FIG. 1 is a schematic front view illustrating a double eyelid formation tape according to an embodiment of the present invention.
Figure 2:
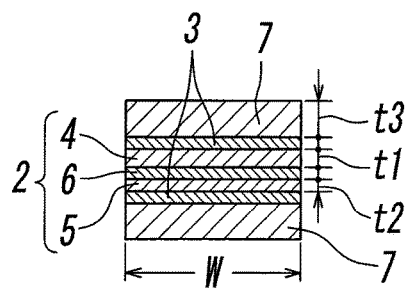
FIG. 2 is an enlarged cross-sectional view of the double eyelid formation tape illustrated in FIG. 1 taken along line D-D.
Figure 3:
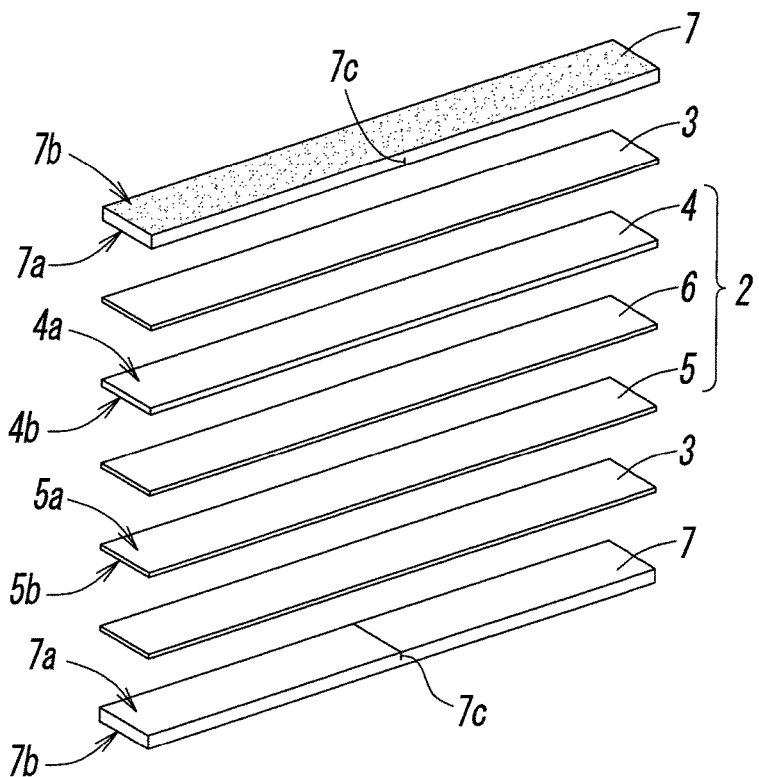
FIG. 3 is an exploded perspective view of the double eyelid formation tape illustrated in FIG. 1.

As illustrated in FIGS. 1 to 3, a double eyelid formation tape 1 according to the present invention is formed by applying a first adhesive 3, which is used for attaching a tape-shaped member 2 to a skin of an eyelid, onto the two surfaces of the tape-shaped member 2, which has elastic contractility when the tape-shaped member 2 is stretched to a length to be used, that is, a predetermined length suitable for an operation of attaching the double eyelid formation tape 1 to the eyelid. The double eyelid formation tape 1 is used for forming a double eyelid by utilizing the above-mentioned elastic contractility of the tape-shaped member 2. The tape-shaped member 2 is formed of a multilayer body that includes first and second base material layers 4 and 5, each of which is made of a resin, and formed so as to have an elongated tape shape and a central axis 1 linearly extending in the longitudinal direction of the tape-shaped member 2. In addition, the tape-shaped member 2 is formed in such a manner that, when the tape-shaped member 2 is stretched by being pulled to the above-mentioned predetermined length, the entire length of the tape-shaped member 2 will not return to the original length of the tape-shaped member 2 before being pulled even if the force that pulls the tape-shaped member 2 is removed, that is, the tape-shaped member 2 is maintained in a state of being irreversibly and permanently deformed (such deformation of the tape-shaped member 2 and the base material layers 4 and 5 will hereinafter be referred to as "plastic deformation", and to cause the plastic deformation by stretching the tape-shaped member 2 and the base material layers 4 and 5 and to cause the tape-shaped member 2 and the base material layers 4 and 5 to transition to the plastic zone will hereinafter be referred to as "extending"). In the present application, the term "elastic contractility" of the tape-shaped member 2 and the base material layers 4 and 5 only refers to, among contraction that occurs when the tape-shaped member 2 and the base material layers 4 and 5 are extended by being pulled, and then the pulling force is removed, substantially momentary contraction with an elastic contractive force. Note that it is not essential that the axis 1 of the tape-shaped member 2 extend linearly as described above, and the axis 1 may be somewhat curved or the like as long as the use of the tape-shaped member 2 by stretching the tape-shaped member 2 is not obstructed.

Figure 15:
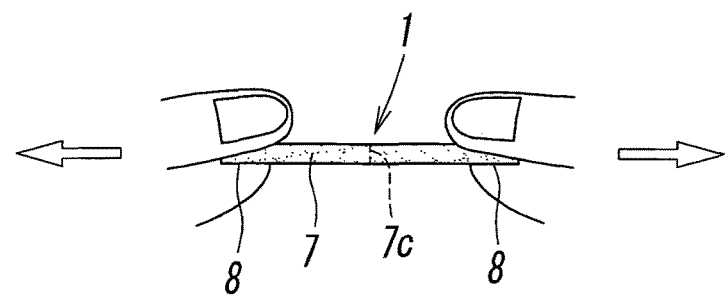
FIG. 15 is a schematic diagram 1 illustrating a method for forming the double eyelid according to the present invention.
Figure 16:
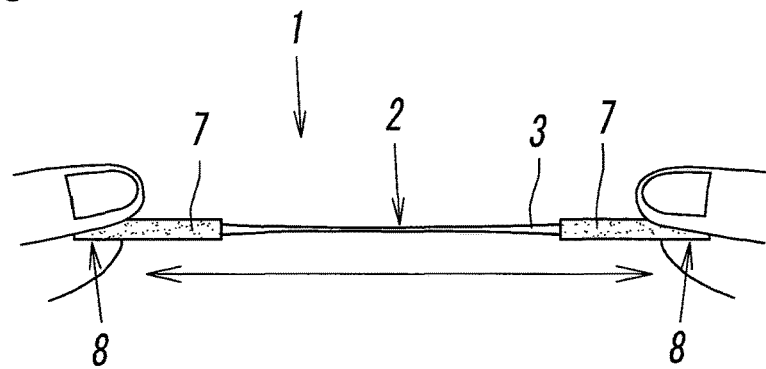
FIG. 16 is a schematic diagram 2 illustrating the method for forming the double eyelid according to the present invention.
Figure 17:
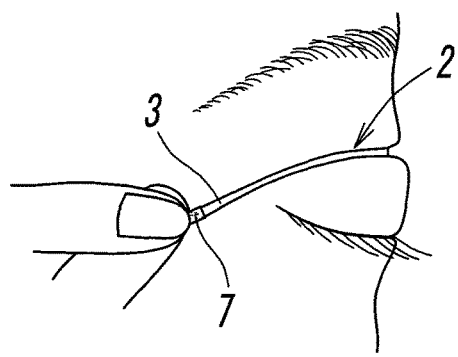
FIG. 17 is a schematic diagram 3 illustrating the method for forming the double eyelid according to the present invention.
Figure 18:
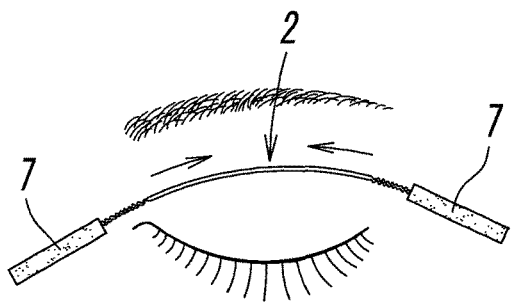
FIG. 18 is a schematic diagram 4 illustrating the method for forming the double eyelid according to the present invention.
Figure 19:
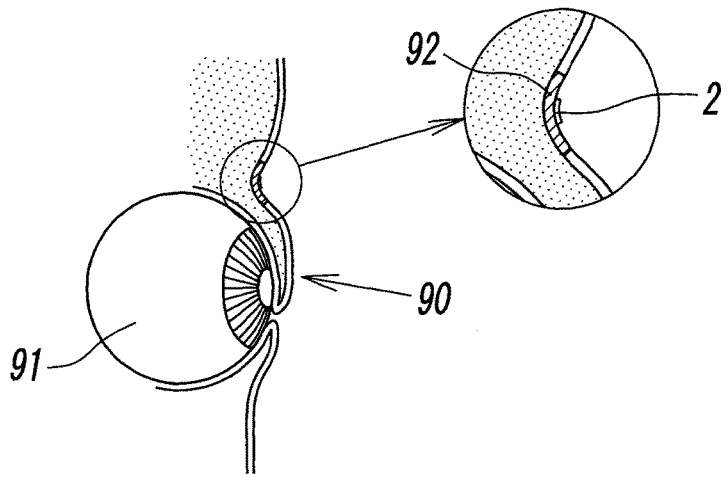
FIG. 19 is a schematic diagram 5 illustrating the method for forming the double eyelid according to the present invention.
Figure 20:
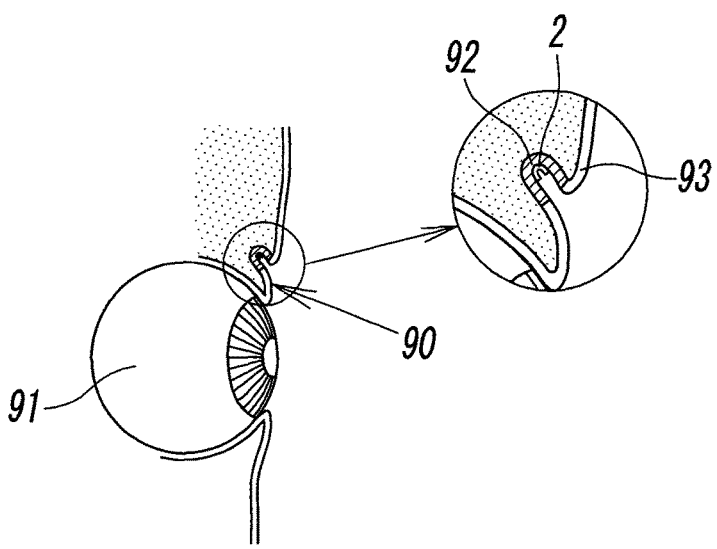
FIG. 20 is a schematic diagram 6 illustrating the method for forming the double eyelid according to the present invention.
Figure 21:
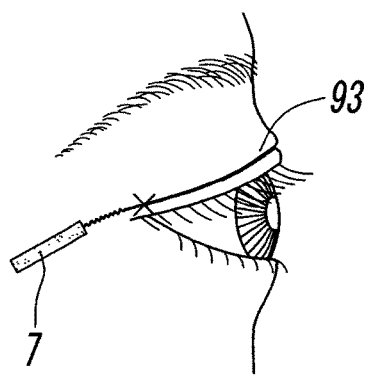
FIG. 21 is a schematic diagram 7 illustrating the method for forming the double eyelid according to the present invention.

When the double eyelid formation tape 1 is used, end portions of the tape-shaped member 2 are held by fingertips, and the tape-shaped member 2 is extended by being pulled to the above-mentioned predetermined length in the longitudinal direction of the tape-shaped member 2. In this state, the tape-shaped member 2 is pressed against an eyelid at a position at which a fold of a double eyelid is desired to be formed and attached to the eyelid with the first adhesive 3 (FIG. 15 to FIG. 17). After that, the force that pulls the tape-shaped member 2 is removed, and then, along with elastic contraction of the tape-shaped member 2, the eyelid contracts by following the shape of the tape-shaped member 2. However, in this case, since the surface of the eyelid is a surface outwardly curved in a convex manner so as to follow the shape of the eyeball, the tape-shaped member 2, which has contracted, slightly digs into the eyelid and forms a neck portion that follows the shape of the tape-shaped member 2 and has a recessed groove shape in the eyelid (FIG. 18 to FIG. 19). As a result, when opening the eyelid, the eyelid is folded at the neck portion (a portion of the skin of the eyelid above the neck portion is folded back in a downward direction at the neck portion) so that a fold of a double eyelid is formed (FIG. 20 to FIG. 21). In other words, it can be said that the tape-shaped member 2 has elastic contractility that contributes to formation of a double eyelid by acting in the above-described manner when the tape-shaped member 2 is extended by being pulled to the predetermined length.

As described above, the double eyelid formation tape 1 that is used for forming a fold of a double eyelid by utilizing the elastic contractility of the tape-shaped member 2, which is obtained after the tape-shaped member 2 is extended, is excellent in terms of convenience and operability for the following reasons. A natural double eyelid can be formed by an extremely simple operation, the operation including stretching the tape-shaped member by holding the end portions of the tape-shaped member, attaching the tape-shaped member to an eyelid by pressing the tape-shaped member against the eyelid while the tape-shaped member is stretched, and releasing the end portions. The double eyelid formation tape 1 can be compactly stored before use, and when the double eyelid formation tape 1 is used, the elastic contractility that contributes to formation of a double eyelid can be obtained by extending the tape-shaped member 2 by pulling the tape-shaped member 2. The double eyelid formation tape 1 can be easily attached to an eyelid because the double eyelid formation tape 1 is pressed against the eyelid while the base material tape, which has been extended, is maintained in a pulled state. In addition, in a state where the double eyelid formation tape 1 is attached to an eyelid, the tape-shaped member 2 that has become thin as a result of being stretched is positioned at the bottom of a neck portion formed in the eyelid, and thus, it is not likely that the tape-shaped member 2, which is attached to the eyelid, will be noticed. Furthermore, the tape-shaped member 2 has elastic stretchability not only in a state of being stretched to the above-mentioned predetermined length but also in a state of being attached to an eyelid and is capable of expanding and contracting while following movement of the eyelid, and thus, the double eyelid formation tape 1 has an advantage in that it is less likely to provide an uncomfortable feeling to a user and the like.

In order to improve, while making good use of its excellent advantages, such a double eyelid formation tape, which utilizes the elastic stretchability of the tape-shaped member obtained after extending the tape-shaped member, in such a manner that the double eyelid formation tape can be widely used for eyelids in various states including an eyelid that will easily become a double eyelid and an eyelid that is less likely to become a double eyelid, it is necessary that the tape-shaped member 2 have, in a good balance, a maximum elastic contractive force (elastic contractive force that is generated when the tape-shaped member is stretched to a predetermined length) large enough for the tape-shaped member 2 to contract by resisting the large tension of an eyelid (the resistance force of the eyelid that tries to push back the tape-shaped member that contracts and tries to dig into the eyelid) and an elastic contraction percentage (elastic contraction amount) that enables a neck portion, which has a suitable depth required for forming a natural fold of a double eyelid, to be formed. Accordingly, in order to obtain a larger maximum elastic contractive force, it is necessary to increase the cross-sectional area of the tape-shaped member. However, in contrast, in order to make the double eyelid formation tape 1 unnoticeable when the double eyelid formation tape 1 is attached to an eyelid, it is desirable that the cross-sectional area be kept as small as possible.

In the double eyelid formation tape 1 according to the present invention, the tape-shaped member 2 is formed of a multilayer body that includes the first base material layer 4, which is made of a synthetic resin other than an elastomer resin, and the second base material layer 5, which has an excellent elastic contraction characteristic when the second base material layer 5 is stretched and which is made of an elastomer resin. However, the first base material layer 4 is formed so as to be caused to transition to (be extended to) the plastic zone and have an elastic contractility even in the plastic zone when the tape-shaped member 2 is stretched to the above-mentioned predetermined length.

With this configuration, the tape-shaped member 2 can obtain an elastic contractive force and an elastic contraction percentage with which the tape-shaped member 2 can contract by resisting the large tension of an eyelid that is less likely to become a double eyelid and form a neck portion having a necessary depth while an increase in the total cross-sectional area of the first and second base material layers 4 and 5 is suppressed.

On the other hand, the second base material layer 5, which is made of an elastomer resin, is formed so as to have a maximum elastic contractive force smaller than the maximum elastic contractive force of the first base material layer 4, and a balance between the second base material layer 5 and the first base material layer 4 is achieved by, for example, setting the cross-sectional area of the second base material layer 5 to be sufficiently smaller than the cross-sectional area of the first base material layer 4 in such a manner that the maximum elastic contractive force and the elastic contraction percentage will not be unnecessarily large. In order to achieve the balance between the second base material layer 5 and the first base material layer 4 with more certainty, it is desirable that the maximum elastic contractive force of the second base material layer 5 be half of the maximum elastic contractive force of the first base material layer 4 or smaller.

The multilayer structure of the tape-shaped member 2 will now be specifically described. In the present embodiment, the tape-shaped member 2 is formed of a multilayer body that has a two-layer structure and that includes a first base material piece, which is formed of a single layer film made of a synthetic resin other than an elastomer resin and which serves as the first base material layer 4, and a second base material piece, which is formed of a single layer film made of an elastomer resin and which serves as the second base material layer 5.

The first base material piece 4 has a first surface 4*a* and a second surface 4*b*, which is opposite to the first surface 4*a*, and similarly, the second base material piece 5 has a first surface 5*a* and a second surface 5*b*, which is opposite to the first surface 5*a*. The first adhesive 3 is applied to the first surface 4*a* of the first base material piece 4 and the second surface 5*b* of the second base material piece 5. The tape-shaped member 2 is formed of a multilayer body that includes the first and second base material pieces 4 and 5 and that is formed by bonding the second surface 4b of the first base material piece 4 and the first surface 5a of the second base material piece 5 with a second adhesive 6.

By interposing the second adhesive 6 between the first base material piece 4 and the second base material piece 5 as described above, when the tape-shaped member 2 is stretched, or when the tape-shaped member 2 is pressed against an eyelid, part of the second adhesive 6 is pushed onto a surface of the tape-shaped member 2 and can be expected to contribute to the attachment of the tape-shaped member 2 onto the eyelid together with the first adhesive 3.

In the present embodiment, the first and second base material pieces 4 and 5 are formed so as to have the same width W and the same length L, and accordingly, the tape-shaped member 2 also has the width W and the length L.

Note that the first adhesive 3 may be applied onto only one surface of the tape-shaped member 2, and in this case, the first adhesive 3 may be applied onto only the first surface 4a of the first material piece 4 or the second surface 5b of the second material piece 5. In addition, the first adhesive 3 is not necessarily be applied over the entire two surfaces or the entire one surface of the tape-shaped member 2 as in the present embodiment, and for example, the first adhesive 3 may be applied to at least an intermediate portion, which is to be actually attached to an eyelid, excluding the end portions (portions to be held), which are to be held by fingertips when the double eyelid formation tape 1 is used.

From the standpoint of manufacturing the first base material piece 4 and the second base material piece 5, which will be described later, it is desirable that the width W and the length L of the first base material piece 4 be the same as the width W and the length L of the second base material piece 5, respectively, as in the present embodiment. However, the widths W are not necessarily be the same as each other, and the lengths L are not necessarily be the same as each other. The widths W of the base material pieces 4 and 5 may be different from each other, and the lengths L of the base material pieces 4 and 5 may be different from each other as long as the operation and the functions of the double eyelid formation tape 1 are not be obstructed.

The first base material layer 4 and the second base material layer 5 are not necessarily be stacked one on top of the other with the second adhesive 6 interposed therebetween as in the present embodiment, and for example, the base material layers 4 and 5 may be integrally formed by directly joining the second surface 4b of the first base material layer 4 and the first surface 5a of the second base material layer together by, for example, applying the second base material layer to the second surface 4b of the first base material layer 4 and causing the second base material layer to solidify or by integrating the base material layers 4 and 5 together by hot pressing.

Examples of the above-mentioned synthetic resin include vinyl chloride resin, polyolefin resin, and the like that can be easily stretched by using fingertips and caused to transition to (extended to) the plastic zone and that have elastic stretchability even in the plastic zone. It is preferable that a polyethylene be used as the synthetic resin, and it is particularly preferable that low-density polyethylene be used as the synthetic resin. Although it will be described later, it is desirable that, when the first base material piece 4 is axially stretched in the manufacture of the film, which forms the first base material piece 4, the first base material piece 4 not be stretched or be stretched at an extremely low stretching magnification particularly in the longitudinal direction thereof (axis 1 direction).

On the other hand, examples of the above-mentioned elastomer resin include a latex, synthetic resins (e.g., EVA and polyurethane), and the like that can be easily stretched by using fingertips and that have an excellent elastic contraction percentage, and among these material, it is particularly preferable that polyurethane be used as the elastomer resin.

Note that an additive, such as pigment or a glitter material, may be added to the above-mentioned synthetic resin and the above-mentioned elastomer resin as necessary.

Considering, for example, the operability of the tape-shaped member 2 and the first and second base material layers 4 and 5 in practical use and the widths of the tape-shaped member 2 and the first and second base material layers 4 and 5 after being extended, that is, the widths of the tape-shaped member 2 and the first and second base material layers 4 and 5 when attached to an eyelid, it is preferable that the widths W of the tape-shaped member 2 and the first and second base material layers 4 and 5 each be within a range of 0.6 mm to 1.4 mm and that the lengths L of the tape-shaped member 2 and the first and second base material layers 4 and 5 each be within a range of 20 mm to 35 mm, and it is further preferable that the lengths L each be within a range of 25 mm to 30 mm. Although the thickness t1 of the first base material layer 4 and the thickness t2 of the second base material layer 5 should be set, for example, on the basis of the cross-sectional areas of the base material layers due to the relationship with the width W, considering the thickness of each of the first and second base material layers 4 and 5 after being extended, that is, the thickness of each of the first and second base material layers 4 and 5 when attached to an eyelid, and the like, it is desirable that the sum of t1 and t2 be within a range of 50 μm to 100 μm. In particular, in the case where the above-mentioned synthetic resin and the above-mentioned elastomer resin are respectively low-density polyethylene and polyurethane, it is desirable that the thickness t2 of the second base material layer 5 be sufficiently smaller than the thickness t1 of the first base material layer 4, and for example, it is desirable that the thickness t1 of the first base material layer 4 be within a range of 70 μm to 80 μm, the thickness t2 of the second base material layer 5 be within a range of 7 μm to 9 μm, the width W of each of the base material layers 4 and 5 be within a range of 0.8 mm to 1.2 mm, and the length L of each of the base material layers 4 and 5 be within a range of 25 mm to 30 mm. This combination of low-density polyethylene, which is used as the synthetic resin, and polyurethane, which is used as the elastomer resin, is preferable because they both have excellent breathability as well as excellent characteristics for forming a double eyelid.

Note that, although a dermatological acrylic adhesive is preferably used as the first and second adhesives 3 and 6, the first and second adhesives 3 and 6 are not limited to such a dermatological acrylic adhesive and any adhesive may be used as long as it can be applied on skin. In addition, the three adhesives, which are the first adhesives 3 and 3 and the second adhesive 6, may be different from one another.

As illustrated in FIG. 1 to FIG. 4, the double eyelid formation tape 1 further includes release sheet pieces 7 each of which is attached to the first adhesive 3, which is applied to the tape-shaped member 2, in such a manner as to entirely cover the first adhesive 3 and each of which has a property of being easily released from an adhesive. The release sheet pieces 7 protect the first adhesive 3 before the double eyelid formation tape 1 is used, and when the double eyelid formation tape 1 is used, the release sheet pieces 7 form holding portions 8 and 8 that do not have a viscosity and that are used for holding the end portions of the tape-shaped member 2 by fingertips and operating the tape-shaped member 2.

In the present embodiment, the release sheet pieces 7 are disposed on the two surfaces of the tape-shaped member 2. Each of the release sheet pieces 7 is formed so as to have the width W and the length L, which are the same as those of the tape-shaped member 2, and has an inner surface 7*a*, which is attached to the first adhesive 3, and an outer surface 7*b*, which is opposite to the inner surface 7*a*. An easily-tearable portion 7*c* is formed in a center portion of each of the release sheet pieces 7 in the longitudinal direction (axis 1 direction) in such a manner as to be easily torn as a result of being pulled in the longitudinal direction. End portions of the release sheet piece 7 on opposite sides of the easily-tearable portion 7*c* in the longitudinal direction form the pair of holding portions 8 and 8, which are used for stretching the tape-shaped member 2 in the longitudinal direction when the double eyelid formation tape 1 is used.

Consequently, when the tape-shaped member 2 is pulled in the longitudinal direction by holding the pair of holding portions 8 and 8 by fingertips, each of the release sheet pieces 7 tears at the easily-tearable portion 7*c*, and an intermediate portion of the release sheet piece 7, which is positioned between the pair of holding portions 8 and 8, separates from the first adhesive 3. As a result, the intermediate portion of the tape-shaped member 2 from which the release sheet pieces 7 and 7 have separated can be stretched.

More specifically, each of the release sheet pieces 7 is integrally formed of a silicone resin that has a property of being easily released from an adhesive and tearability in the easily-tearable portion 7*c*. Regarding this silicone resin, it is preferable that the hardness of the silicone resin be high because the silicone resin is more likely to have better tearability, which is mentioned above, as its hardness becomes higher, and it is desirable that the thickness t3 of the silicone resin be within a range of about 0.3 mm to about 0.5 mm.

Figure 4:
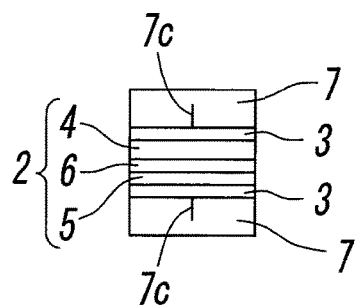
FIG. 4 is an enlarged view of a portion IV of the double eyelid formation tape illustrated in FIG. 1 including a tearable portion.

In the present embodiment, as illustrated in FIG. 4, each of the easily-tearable portions 7*c* is formed of a linear score that is formed by cutting the corresponding release sheet piece 7 from the inner surface 7*a* of the release sheet piece 7, which is in contact with the first adhesive 3, to halfway through the release sheet piece 7 in the thickness direction of the release sheet piece 7 and that extends in the lateral direction, so that the easily-tearable portion 7*c* is prevented from being torn before the double eyelid formation tape 1 is used due to carelessness.

The inner surface 7*a* and the outer surface 7*b* of each of the release sheet pieces 7 are respectively formed so as to be a mirror-finished surface and a finely roughened surface, and by inverting the release sheet pieces 7 during the manufacturing process so as to change the surfaces of the release sheet pieces 7 that are brought into contact with the adhesive 3, the releasability of the release sheet pieces 7 with respect to the adhesive 3 can be adjusted.

Note that each of the release sheet pieces 7 is not necessarily be integrally formed of a silicone resin and may be, for example, a release sheet formed by forming an easily-releasable layer, which is made of a silicone resin, on a sheet. In addition, each of the easily-tearable portions 7*c* is not necessarily be the above-mentioned score (formed by half cutting) and may be, for example, a notch having a V-shape.

Tensile tests performed on a first sample tape SA that is made of the above-mentioned synthetic resin, a second sample tape SB that is made of the above-mentioned elastomer resin, and a third sample tape SC that is formed of the first and second sample tapes SA and SB stacked one on top of the other and the results of the tensile tests will now be described with reference to FIG. 5 to FIG. 7.

Figure 6:
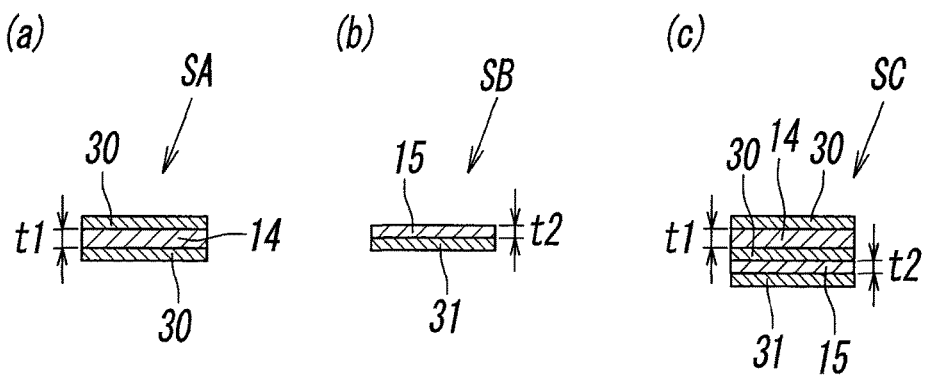
FIGS. 6(a) to 6(c) are sectional views illustrating configurations of samples used in the tensile tests shown in FIG. 5.

First, these three types of sample tapes S (SA, SB, and SC), which are illustrated in FIG. 6, were prepared. As illustrated in FIG. 6(*a*), the first sample tape SA is formed by applying adhesives 30 and 30 to the two surfaces of a base material tape 14 (thickness t1=75 μm) that has a single layer and that is made of low-density polyethylene, which is used as the above-mentioned synthetic resin, and the first sample tape SA is formed by using a base material tape with an adhesive that is the same as a working product according to Patent Document 9, which has been previously proposed. As illustrated in FIG. 6(*b*), the second sample tape SB is formed by applying an adhesive 31 to one surface of a base material tape 15 (thickness t2=8 μm) that has a single layer and that is made of polyurethane, which is used as the above-mentioned elastomer resin. As illustrated in FIG. 6(*c*), the third sample tape SC is formed of the first and second sample tapes SA and SB stacked one on top of the other and has a two-layer structure that is the same as the two-layer structure, which has been described above in the present embodiment and in which the first adhesives 3 and 3 are applied to the two surfaces of the tape-shaped member 2.

Note that each of the sample tapes S (SA, SB, and SC), had a width Ws of 10 mm and a length Ls of 50 mm. Each of the adhesives 30 and 31 is a dermatological acrylic adhesive.

Figure 7:
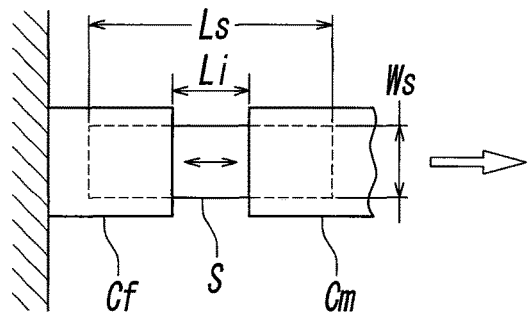
FIG. 7 is a schematic diagram illustrating a method for conducting the tests shown in FIG. 5 and FIG. 8.

Next, as illustrated in FIG. 7, end portions of each of the sample tapes S were held by a pair of chucks Cf and Cm of a tensile testing machine, which are disposed in such a manner as to face each other with a gap of 10 mm therebetween. In other words, an initial length Li of each of the tapes, which are to be stretched, was set to 10 mm. Then, each of the sample tapes S was stretched to the above-mentioned "predetermined length" by moving the chuck Cm in a direction (right direction in FIG. 7) away from the chuck Cf, which was fixed in place, at a speed of 50 mm/s to a maximum displacement point (le), which was 70 mm. In other words, in these tests, the above-mentioned "predetermined length" was set to 80 mm, which was a value obtained by adding 70 mm, which was a maximum displacement amount, to the initial length Li (=10 mm). Immediately after that, the chuck Cm was moved in a direction (left direction in FIG. 7) toward the chuck Cf at a speed of 100 mm/s and returned to its initial position. During the above operation, a test force at each displacement point of the chuck Cf was measured. The results of such measurements performed on the sample tapes SA, SB, and SC are shown in FIG. 5.

Figure 5:
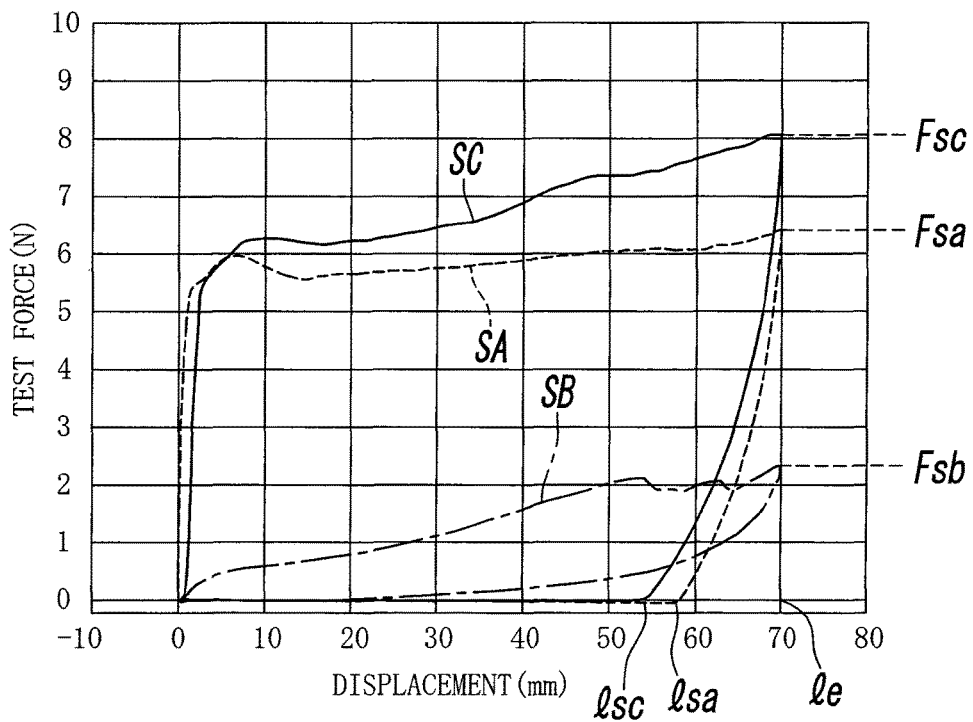
FIG. 5 is a graph showing results of tensile tests of various tapes to be used for forming the double eyelid formation tape according to the present invention.

As shown in the measurement results in FIG. 5, a maximum elastic contractive force Fsc of the third sample tape SC when the third sample tape SC is stretched to the predetermined length, which is 80 mm, is approximately equal to the sum of a maximum elastic contractive force Fsa of the first sample tape SA and a maximum elastic contractive force Fsb of the second sample tape, and the maximum elastic contractive force Fsc is realized by setting a base material thickness to 83 μm.

On the other hand, as the maximum elastic contractive force Fsc is large, the increase in the elastic contraction percentage (amount of elastic contraction: le−lsc) of the third sample tape SC is larger than the increase in the elastic contraction percentage (amount of elastic contraction:

le–lsa) of the first sample tape SA. The influence of the large elastic contraction percentage of the second sample tape SB on the increase in the elastic contraction percentage of the third sample tape SC is negligible, and it can be said that the increase in the elastic contraction percentage of the third sample tape SC remains within a reasonable range and is preferable.

Here, in the present application, an elastic contraction region of the tape-shaped member, which is used for forming a double eyelid, means the elastic contraction region from le to lsc of the third sample tape SC.

Tensile tests performed on a fourth sample tape A that is a working product according to Patent Document 9, which has been proposed previously, a fifth sample tape B that is a reference example, and a sixth sample tape C that is an example of the present invention and the results of the tensile tests will now be described with reference to FIG. 8 and FIG. 9.

Figure 9:
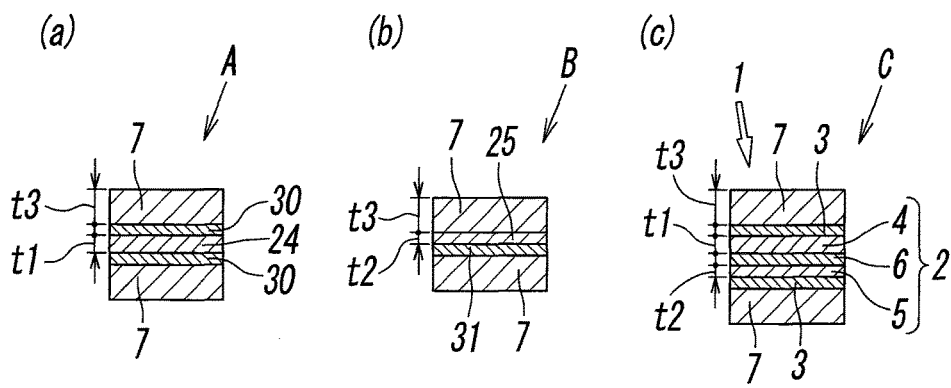
FIGS. 9(a) to 9(C) are sectional views illustrating configurations of samples used in the tensile tests shown in FIG. 8.

First, as illustrated in FIG. 9(*a*), the fourth sample tape A was formed by applying the adhesives 30 and 30 to the two surfaces of a base material tape piece 24 (thickness t1=75 μm) that has a single layer and that is made of low-density polyethylene, which is used as the above-mentioned synthetic resin, and attaching the release sheet pieces 7 and 7 (thickness t3=0.3 mm) to the adhesives 30 and 30 and was formed so as to have a width Ws of 1.2 mm and a length Ls of 28 mm. As illustrated in FIG. 9(*b*), the fifth sample tape B was formed by applying the adhesive 31 to one surface of a base material tape piece 25 (thickness t2=8 μm) that has a single layer and that is made of polyurethane, which is used as the above-mentioned elastomer resin, and attaching the release sheet pieces 7 (thickness t3=0.3 mm) to the adhesive 31 and a surface of the base material tape 25 on the side opposite to the adhesive 31. This configuration was employed in order to hold the fifth sample tape B by the chucks Cf and Cm, which are illustrated in FIG. 7, with certainty during the tests. Note that the fifth sample tape B was formed so as to have a width Ws of 1.2 mm and a length Ls of 28 mm. As illustrated in FIG. 9(*c*), the sixth sample tape C was formed so as to have a configuration similar to that in the embodiment illustrated in FIG. 1 to FIG. 4 by using tape members (respectively made of low-density polyethylene and polyurethane), which are respectively the same as the base material tape piece 24 of the fourth sample tape A and the base material tape piece 25 of the fifth sample tape B, as the first base material piece 4 (thickness t1=75 μm) and the second base material piece 5 (thickness t2=8 μm), respectively, by using one of the adhesives 30 and 30 as the second adhesive 6 and the other one of the adhesives 30 and 30 and the adhesive 31 as the first adhesives 3 and 3, and by attaching the release sheet pieces 7 (thickness t3=0.3 mm) to the adhesives 3 and 3. Note that the sixth sample tape C was formed so as to have a width Ws of 0.9 mm and a length Ls of 28 mm.

Next, similar to the cases of the first to third sample tapes S (SA, SB, and SC), tensile tests were performed on the fourth to sixth sample tapes S (A, B, and C) by the method illustrated in FIG. 7. The results of the tensile tests are shown in the graph of FIG. 8.

Figure 8:
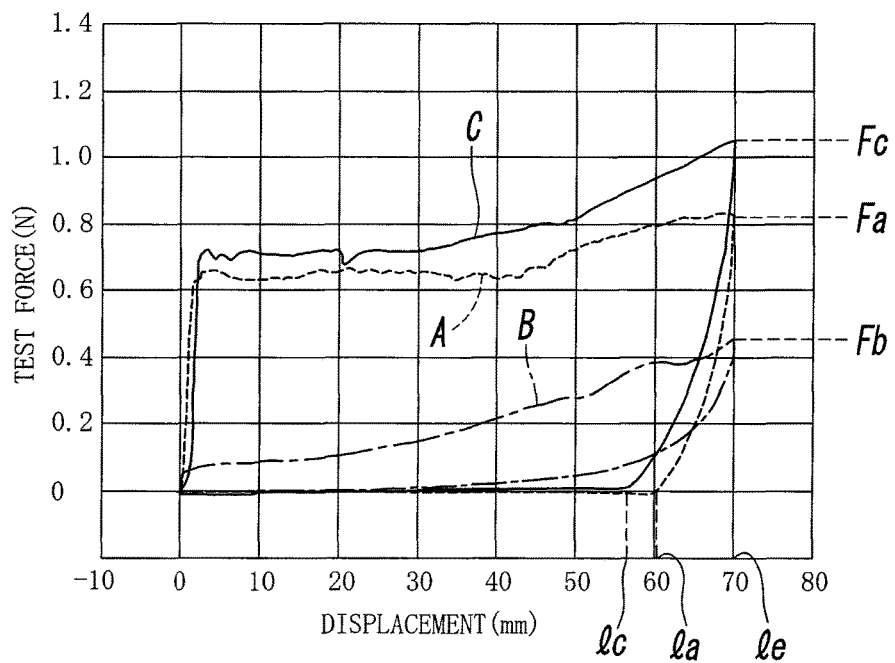
FIG. 8 is a graph showing results of tensile tests conducted to compare an example of the present invention and an example of a publicly known technique.

It was found from the measurement results in FIG. 8 that, although the cross-sectional area of the base material layer of the sixth sample tape C, which was an example of the present invention, was smaller than the cross-sectional area of the base material layer of the fourth sample tape A, which was a working product according to Patent Document 9 proposed previously, a maximum elastic contractive force Fc and the elastic contraction percentage (amount of elastic contraction: le–lc) of the sixth sample tape C was reasonably larger than a maximum elastic contractive force Fa and the elastic contraction percentage (amount of elastic contraction: le–la) of the fourth sample tape A, and that the sixth sample tape C could be more widely used for eyelids in various states than the fourth sample tape A.

Here, in the present application, it is obvious that the elastic contraction region of the tape-shaped member, which is used for forming a double eyelid, means the elastic contraction region from le to lc of the sixth sample tape C (example of the present invention) as described above.

Note that, when test subjects actually used the fourth and sixth sample tapes A and C to check the effects of the tapes, it was confirmed that some of the test subjects who could not form a double eyelid by using the fourth sample tape A were able to form a double eyelid by using the sixth sample tape C. At that time, the sixth sample tape C did not provide an uncomfortable feeling to the test subjects and had a good usability.

A method for manufacturing the double eyelid formation tape according to the present invention will now be described in detail with reference to FIG. 10 to FIG. 14.

Figure 10:
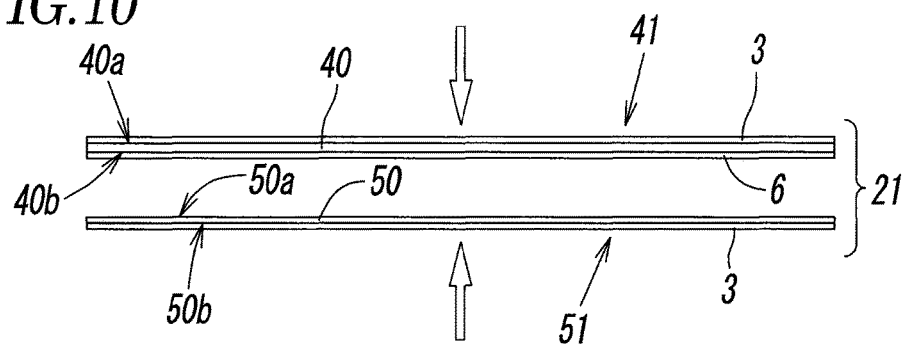
FIG. 10 is a schematic diagram 1 illustrating a process of manufacturing the double eyelid formation tape according to the present invention.

First, as illustrated in FIG. 10, a double-sided adhesive sheet 41 that is formed by applying the first adhesive 3 and the second adhesive 6 each of which is, for example, a dermatological acrylic adhesive, to a first surface 40*a* and a second surface 40*b*, which is opposite to the first surface 40*a*, of a first base material sheet 40, respectively, is prepared. The first base material sheet 40 is made of a synthetic resin other than an elastomer resin, such as vinyl chloride resin or polyolefin resin, is caused to transition to (be drawn to) the plastic zone when the first base material sheet 40 is stretched to the above-mentioned predetermined length, and has an elastic contractility even in the plastic zone. In addition, a single-sided adhesive sheet 51 that is formed by applying the first adhesive 3, which is, for example, a dermatological acrylic adhesive as well, to a second surface 50*b* of a second base material sheet 50 that is made of an elastomer resin, such as an EVA resin or a polyurethane resin, and that has a first surface 50*a* and the second surface 50*b*, which is opposite to the first surface 50*a*, is prepared. Then, the first base material sheet 40 and the second base material sheet 50 are stacked one on top of the other by bonding the second surface 40*b* of the first base material sheet 40 and the first surface 50*a* of the second base material sheet 50 with the second adhesive 6, so that a double-sided adhesive multilayer sheet 21 is fabricated.

Note that, although the first adhesive 3 and the second adhesive 6 of the double-sided adhesive sheet 41 are treated as different adhesives in terms of their functions, the first adhesive 3 and the second adhesive 6 may be the same adhesive. In addition, although the first adhesive 3 of the double-sided adhesive sheet 41 and the first adhesive 3 of the single-sided adhesive sheet 51 are treated as the same adhesive in terms of their functions, the first adhesives 3 and 3 may be different adhesives.

Figure 11:
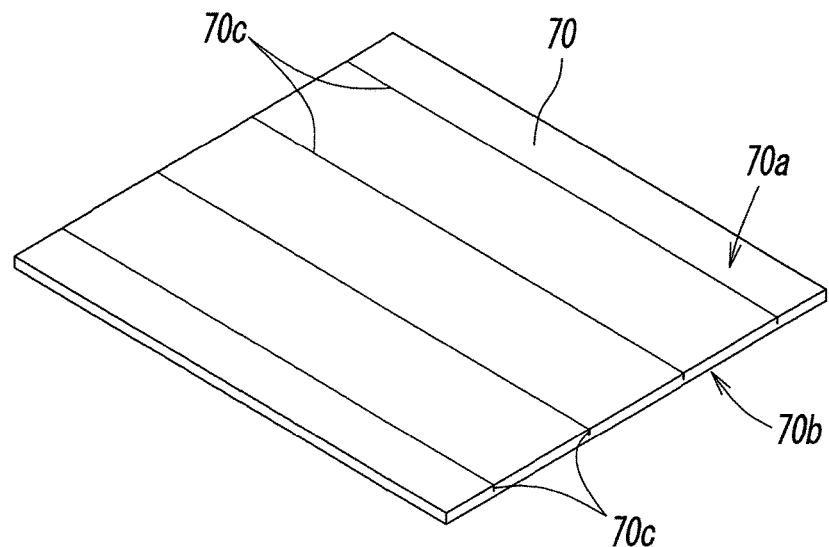
FIG. 11 is a schematic diagram 2 illustrating the process of manufacturing the double eyelid formation tape according to the present invention.

On the other hand, as illustrated in FIG. 11, release sheets 70 each of which has a first surface 70*a*, which is a mirror-finished surface, and a second surface 70*b*, which is opposite to the first surface 70*a* and which is a roughened surface, are formed by thermoforming a silicone resin, which has high hardness, and easily-tearable lines 70*c* that are parallel to one another and equally spaced are formed in the first surfaces 70*a* by cutting the release sheets 70 from the first surfaces 70*a* to halfway through release sheets 70 in the thickness direction.

Figure 12:
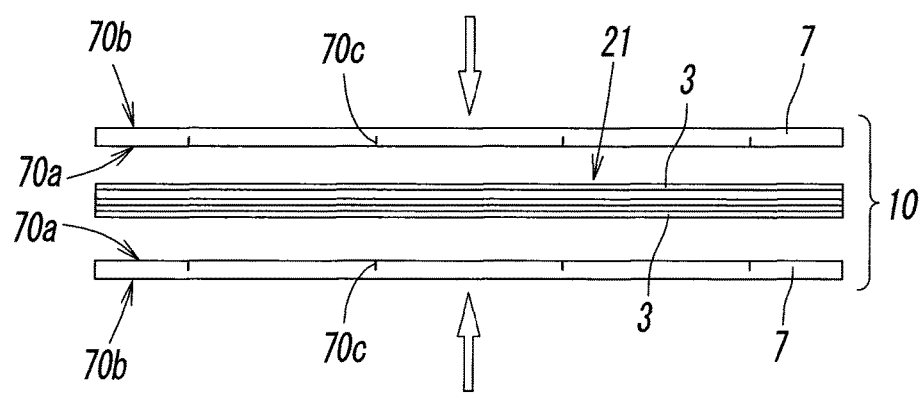
FIG. 12 is a schematic diagram 3 illustrating the process of manufacturing the double eyelid formation tape according to the present invention.

Then, as illustrated in FIG. 12, a multilayer sheet 10 is formed by attaching the first surfaces 70a of the two release sheets 70 to the first adhesives 3 and 3, which are applied to the two surfaces of the double-sided adhesive multilayer sheet 21.

Figure 13:
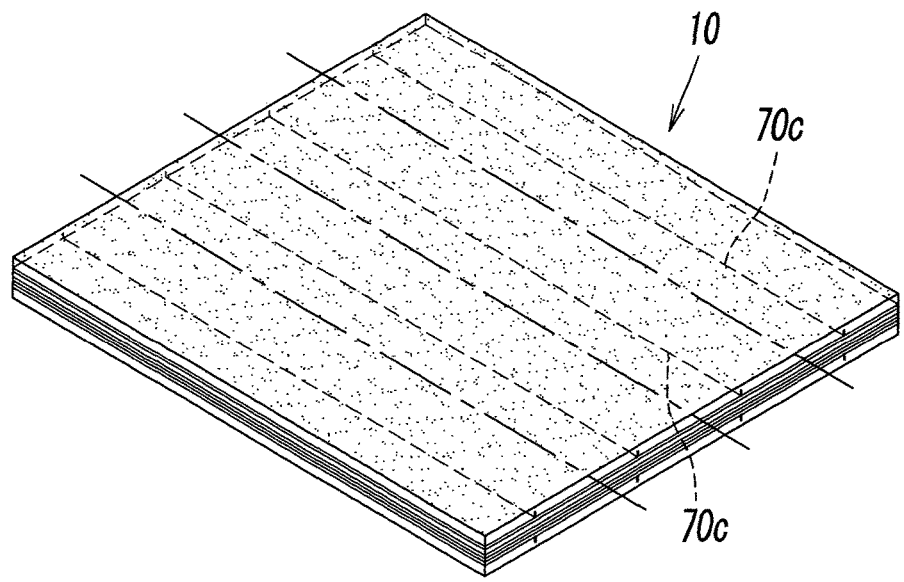
FIG. 13 is a schematic diagram 4 illustrating the process of manufacturing the double eyelid formation tape according to the present invention.
Figure 14:
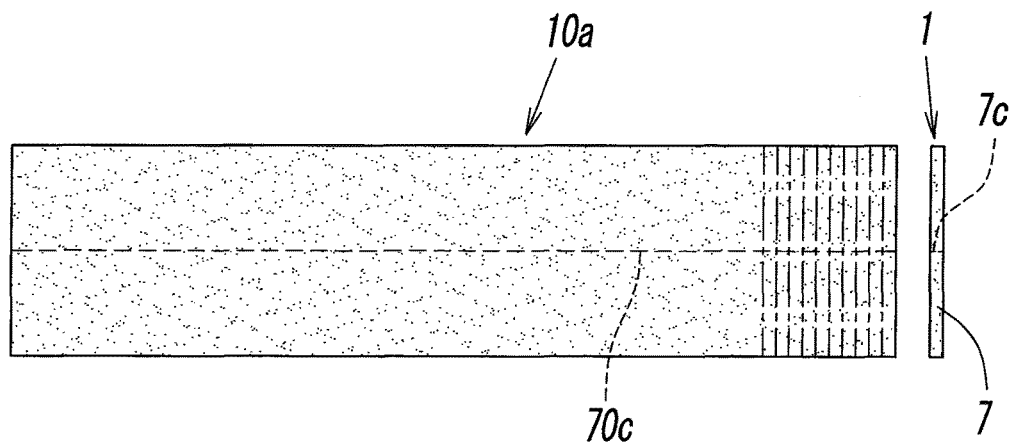
FIG. 14 is a schematic diagram 5 illustrating the process of manufacturing the double eyelid formation tape according to the present invention.

Next, as illustrated in FIG. 13 and FIG. 14, the multilayer sheet 10 is cut at positions in the middle of the adjacent easily-tearable lines 70c in a direction parallel to the easily-tearable lines 70c so as to form multilayer sheets 10a each of which has an elongated strip shape, and the multilayer sheets 10a, each of which has a strip shape, are thinly cut in a direction that crosses at right angles to the easily-tearable lines 70c, so that the double eyelid formation tapes 1 in each of which the easily-tearable portion 7c is positioned in the middle in the longitudinal direction can be obtained.

A method for forming a double eyelid using the double eyelid formation tape 1 will be described in detail below with reference to FIG. 15 to FIG. 21.

First, although not illustrated, oil and the like on an eyelid that is to become a double eyelid are wiped off, and after that, a position on the eyelid at which a fold of a double eyelid is to be formed is checked by using a pusher or the like. Next, as illustrated in FIG. 15, the holding portions 8 and 8, which are the end portions of the double eyelid formation tape 1, are held by fingertips of both hands, while not holding an intermediate portion of the double eyelid formation tape 1 that is at least 1 cm long, and pulled in the longitudinal direction. Then, the release sheet pieces 7 tear at the easily-tearable portions 7c, which are positioned in the middle, and as illustrated in FIG. 16, the tape-shaped member 2 appears while being stretched. When the tape-shaped member 2 is further stretched, the tape-shaped member 2 is extended and brought into a state where the entire length of the tape-shaped member 2 will not return to the original length of the tape-shaped member 2 even if a force that pulls the tape-shaped member 2 is removed, that is, the tape-shaped member 2 becomes plastically deformed.

Then, when the tape-shaped member 2 is stretched to about 5 cm to about 8 cm, the stretching operation is stopped, and as illustrated in FIG. 17, the tape-shaped member 2, which has been stretched, is pressed against a closed eyelid at the position at which a fold of a double eyelid is desired to be formed while exerting a tension on the tape-shaped member 2. The tape-shaped member 2 is attached to the eyelid with the first adhesive 3, and then, the both hand are released from the holding portions 8.

As a result, as illustrated in FIG. 18, the tape-shaped member 2, which has been stretched, elastically contracts, and thus, a skin of the eyelid also contracts by following the shape of the tape-shaped member 2. However, as illustrated in FIG. 19, the skin of the eyelid 90 is a surface outwardly curved in a convex manner so as to follow the shape of the eyeball 91, and thus, the tape-shaped member 2 digs into the eyelid, so that a neck portion 92 that follows the shape of the tape-shaped member 2 and has a recessed groove shape is formed. In this case, the tape-shaped member 2 is in a state of being attached to a bottom portion of the neck portion 92.

After that, when the eyelid 90 is opened as illustrated in FIG. 20 and FIG. 21, the eyelid is naturally folded back at the neck portion 92, and a fold 93 of a double eyelid is formed.

In this case, although superfluous portions of the end portions of the tape-shaped member 2 that are not attached to the skin of the eyelid 90 are in a contracted state while being curled or wavy due to a difference in contraction amount between the first base material layer 4 and the second base material layer 5, the superfluous portions are cut at appropriate positions. After that, the shape of the double eyelid may be adjusted by using a pusher or the like, which is not illustrated.

Although the embodiment and the example of the present invention have been described in detail above, the present invention is not limited to these, and it is obvious that various design changes can be made within the gist of the present invention.

REFERENCE SIGNS LIST 1 double eyelid formation tape
2 tape-shaped member
3 first adhesive
4 first base material layer (first base material piece)
5 second base material layer (second base material piece)
6 second adhesive
7 release sheet piece
7c easily-tearable portion
8 holding portion

The invention claimed is:

1. A double eyelid formation tape comprising:
a tape-shaped member including one or more surfaces, the tape shaped-member having a long length and having elastic contractility when the tape-shaped member is stretched to a predetermined length in a longitudinal direction of the tape-shaped member, the tape-shaped member used to form a double eyelid by utilizing the elastic contractility,
a first adhesive used to attach a tape-shaped member to an eyelid and applied to the one or more surfaces of the tape-shaped member to form the double eyelid formation tape,
wherein the tape-shaped member is formed of a multilayer body that includes a first base material layer, which is made of a synthetic resin other than an elastomer resin, and a second base material layer, which is made of an elastomer resin,
wherein, when the tape-shaped member is stretched to the predetermined length, the first base material layer is caused to transition to a plastic zone and has elastic contractility even in the plastic zone,
wherein a cross-sectional area of the second base material layer is formed smaller than a cross-sectional area of the first base material layer,
wherein the first and second base material layers have a same width over the entire longitudinal direction, and
when the first and second base material layers are stretched to the predetermined length, the second base material layer has a maximum elastic contractive force smaller than the first base material layer, and has an elastic contraction percentage larger than the first base material layer.

2. The double eyelid formation tape according to claim 1, wherein, when the tape-shaped member is stretched to the predetermined length, the first base material layer has a maximum elastic contractive force larger than a maximum elastic contractive force of the second base material layer, and
wherein, when the first and second base material layers are stretched to the predetermined length, a maximum elastic contractive force of the second base material layer is half of a maximum elastic contractive force of the first base material layer or smaller.

3. The double eyelid formation tape according to claim 1, wherein the synthetic resin is polyolefin.

4. The double eyelid formation tape according to claim 3, wherein the synthetic resin and the elastomer resin are respectively polyethylene and polyurethane.

5. The double eyelid formation tape according to claim 1, wherein the multilayer body is formed by bonding the first and second base material layers together with a second adhesive.

6. The double eyelid formation tape according to claim 5, wherein the first base material layer is made of the synthetic resin in a single layer and has a first surface and a second surface, which is opposite to the first surface,
wherein the second base material layer is made of the elastomer resin in a single layer and has a first surface and a second surface, which is opposite to the first surface,
wherein the first adhesive is applied to the first surface of the first base material layer and/or the second surface of the second base material layer, and
wherein the multilayer body includes the first and second base material layers and that is formed by bonding the second surface of the first base material layer and the first surface of the second base material layer together with the second adhesive.

7. The double eyelid formation tape according to claim 1, wherein necking occurs in the first base material layer in the plastic zone.

8. The double eyelid formation tape according to claim 1, wherein an axis of the tape-shaped member linearly extends in the longitudinal direction.

9. The double eyelid formation tape according to claim 1, wherein a pair of holding portions that are to be held and pulled are formed in end portions of the tape-shaped member in the longitudinal direction.

10. The double eyelid formation tape according to claim 9, further comprising:
a release sheet piece that is releasable from an adhesive,
wherein the release sheet piece is attached to the first adhesive of the tape-shaped member and has a tearable portion formed in a center portion of the release sheet piece in a longitudinal direction of the release sheet piece, the tearable portion being configured to be easily torn as a result of being pulled in the longitudinal direction, and the pair of holding portions are formed of end portions of the release sheet piece on opposite sides of the tearable portion in the longitudinal direction, and
wherein, when the tape-shaped member is pulled in the longitudinal direction by holding the pair of holding portions, the release sheet piece tears at the tearable portion, and an intermediate portion of the release sheet piece, which is positioned between the pair of holding portions, separates from the first adhesive.

11. The double eyelid formation tape according to claim 10, wherein the release sheet piece is made of a silicone resin, and
wherein the tearable portion is formed of a linear score that is formed by cutting the release sheet piece from an inner surface of the release sheet piece, which is in contact with the first adhesive, to halfway through the release sheet piece in a thickness direction and that extends in a lateral direction.

12. A method for manufacturing the double eyelid formation tape according to claim 10, the method comprising:
preparing an adhesive sheet that is formed by applying the first adhesive to two surfaces or one surface of a multilayer body that includes a first base material sheet made of the synthetic resin and a second base material sheet made of an elastomer resin;
preparing a release sheet that is releasable from an adhesive and that includes the tearable portion;
manufacturing a multilayer sheet that is formed by attaching the release sheet to the first adhesive of the adhesive sheet; and
manufacturing the double eyelid formation tape by cutting the multilayer sheet into an elongated belt-like shape in such a manner that the tearable portion is positioned in a middle in a longitudinal direction.

13. The manufacturing method according to claim 12, further comprising:
forming the tearable portion by forming a linear score extending from an inner surface of the release sheet piece, which is in contact with the first adhesive, to halfway through the release sheet piece in a thickness direction,
wherein the synthetic resin is polyolefin, and
wherein the release sheet is made of a silicone resin.

14. A method for manufacturing the double eyelid formation tape according to claim 1, the method comprising:
preparing an adhesive sheet that is formed by applying the first adhesive to two surfaces or one surface of a multilayer body that includes a first base material sheet made of the synthetic resin and a second base material sheet made of an elastomer resin; and
manufacturing the double eyelid formation tape by cutting the adhesive sheet into an elongated belt-like shape.

15. The manufacturing method according to claim 14, wherein the synthetic resin is polyolefin.

16. A method for forming a double eyelid using the double eyelid formation tape according to claim 1, the method comprising:
attaching the tape-shaped member to an eyelid with the first adhesive by holding and pulling end portions of the tape-shaped member in the longitudinal direction of the tape-shaped member and pressing the tape-shaped member against the eyelid in a state where the tape-shaped member is stretched to the predetermined length;
forming a neck portion that follows a shape of the tape-shaped member and has a recessed groove shape in the eyelid by removing a force that pulls the tape-shaped member, which has been attached to the eyelid, and causing the eyelid to contract due to elastic contraction of the tape-shaped member; and
forming a fold of a double eyelid as a result of the eyelid being folded back at the neck portion when the eyelid is opened.

* * * * *